United States Patent [19]

De Lacharriere et al.

[11] Patent Number: 5,788,956
[45] Date of Patent: Aug. 4, 1998

[54] ANTIPERSPIRANT COMPOSITIONS COMPRISING SUBSTANCE P ANTAGONISTS

[75] Inventors: Olivier De Lacharriere, Paris; Lionel Breton, Versailles, both of France

[73] Assignee: Société L'Oréal S.A., Paris, France

[21] Appl. No.: 738,910

[22] Filed: Oct. 28, 1996

[30] Foreign Application Priority Data

Oct. 26, 1995 [FR] France .................. 95 12655

[51] Int. Cl.⁶ .................. A61K 7/32; A61K 7/00
[52] U.S. Cl. .................. 424/65; 424/66; 424/67; 424/68; 424/400; 424/401; 424/404
[58] Field of Search .................. 424/65, 66, 67, 424/68, 400, 401, 404

[56] References Cited

U.S. PATENT DOCUMENTS 4,472,305 9/1984 Hansen et al. .................. 530/329

FOREIGN PATENT DOCUMENTS 0522808 1/1993 European Pat. Off. .

Primary Examiner—Shelley A. Dodson
Attorney, Agent, or Firm—Burns, Doane, Swecker & Mathis, L.L.P.

[57] ABSTRACT

Cutaneous perspiration in a human subject is prevented and/or controlled by topically applying to the skin of an individual in need of such treatment, an effective antiperspirant amount of at least one substance P antagonist.

24 Claims, No Drawings

ANTIPERSPIRANT COMPOSITIONS COMPRISING SUBSTANCE P ANTAGONISTS

BACKGROUND OF THE INVENTION

1. Technical Field of the Invention

The present invention relates to cosmetic and/or dermatological compositions comprising substance P antagonists as antiperspirant agents.

2. Description of the Prior Art

Substance P is a known polypeptide chemical component developed and released by a nerve ending. It is implicated, in particular, in the transmission of pain and in diseases of the central nervous system, such as anxiety or schizophrenia, in respiratory and inflammatory diseases, in gastrointestinal diseases, in rheumatic diseases and in certain dermatological diseases.

FR-94/05537, filed May 5, 1994 and assigned to the assignee hereof, describes substance P antagonists which prevent the synthesis and/or the release and/or the binding of substance P in the treatment of sensitive skins. However, it is neither disclosed nor suggested that these substance P antagonists are useful as antiperspirant agents.

The antiperspirant agents generally used in this art, such as, for example, aluminum salts (aluminum hydroxychloride or aluminum/zirconium complex), present the disadvantage of being irritating to the skin and of being difficult to endure, in particular by individuals with sensitive skins. Especially, these individuals experience itching, smarting, warming sensations, stabbing pains, pins and needles and/or red blotches. These signs are often associated with erythemas.

Serious need, therefore, continues to exist for a non-irritating antiperspirant topical composition which can be used, in particular, by individuals with sensitive skins and which exhibits an effectiveness which is equivalent, indeed superior, to those of the prior art.

SUMMARY OF THE INVENTION

The present invention features the formulation of at least one substance P antagonist into topical compositions in effective antiperspirant agent amounts. This invention more especially features the formulation of at least one substance P antagonist into cosmetic or dermatological compositions well suited for preventing and/or controlling cutaneous perspiration in humans.

DETAILED DESCRIPTION OF BEST MODE AND SPECIFIC/PREFERRED EMBODIMENTS OF THE INVENTION

More particularly according to the present invention, the subject compositions are cosmetically and/or dermatologically acceptable, namely, compatible with the skin, the nails and the mucous membranes. The composition containing one or a plurality of substance P antagonists can be applied under the armpits or on the feet, on the hands and on any other cutaneous region of the body susceptible to perspiring. The subject compositions can, in particular, be used for the treatment of excess sweating, such as Frey's syndrome, or for the treatment of scalps.

For a compound or active species to be recognized as a substance P antagonist, it must elicit an antagonist pharmacological activity towards substance P, namely, induce a coherent pharmacological response in at least one of the two following tests:

(i) the antagonist substance must decrease the extravasation of the plasma through the vascular wall induced by capsaicin, or by an antidromic nerve stimulation, or, alternatively;

(ii) the antagonist substance must cause inhibition of the contraction of the smooth muscles induced by the administration of substance P.

In addition, this substance P antagonist can exhibit a selective affinity for the NK1 receptors for tachykinins.

To date, substance P antagonists have been used to treat the diseases indicated above and to treat sensitive skins. Compare, for example, U.S. Pat. No. 4,472,305, U.S. Pat. No. 4,839,465, EP-A-101929, EP-A-333174, EP-A-336230, EP-A-394989, EP-A-443132, EP-A-498069, EP-A-515681, EP-A-517589, WO-A-92/22569, GB-A-2216529, EP-A-360390, EP-A-429366, EP-A-430771, EP-A-499313, EP-A-514273, EP-A-514274, EP-A-514275, EP-A-514276, EP-A-520555, EP-A-528495, EP-A-532456, EP-A-545478, EP-A-558156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099, WO-A-93/09116, EP-A-522808 and WO-A-93/01165.

It has now surprisingly been determined that a connection exists between substance P antagonists and perspiration.

According to the present invention, the one or more substance P antagonists are advantageously selected from among peptides, compounds comprising at least one heterocycle, nitrogenous compounds comprising at least one benzene ring, salts of monovalent, divalent and trivalent cations, extracts of plant or animal origin and mixtures thereof.

The substance P antagonist of the invention can be a peptide or a non-peptide nitrogenous derivative and, more specifically, a compound containing a nitrogenous heterocycle or a nitrogen atom bonded directly or indirectly to a benzene ring or, more preferably, a salt of certain monovalent, divalent and trivalent cations or, alternatively, a mixture of these antagonists.

For example, sendide and spantide II are useful peptide substance P antagonists.

Sendide has the formula:

in which:

Tyr represents tyrosine,

D-Phe represents D-phenylalanine,

Phe represents phenylalanine,

D-His represents D-histidine,

Leu represents leucine,

Met represents methionine.

Spantide II has the formula:

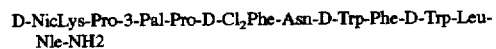

in which:

D-NicLys represents D-lysine nicotinate,

Pro represents proline,

3-Pal represents 3-pyridylalanine,

D-Cl$_2$Phe represents D-dichlorophenylalanine,

Asn represents asparagine,

D-Trp represents D-tryptophan,

Phe represents phenylalanine,

Leu represents leucine,

Nle represents norleucine.

It is also possible to use, as peptide substance P antagonists, the peptides described in U.S. Pat. No. 4,472, 305, U.S. Pat. No. 4,839,465, EP-A-101929, EP-A-333174, EP-A-336230, EP-A-394989, EP-A-443132, EP-A-498069, EP-A-515681, EP-A-517589, WO-A-92/22569 and GB-A-2216529.

The non-peptide substance P antagonists which are suitable per this invention are advantageously compounds comprising a heteroatom bonded directly or indirectly to a benzene ring or contained in a heterocycle. In particular, this heteroatom is an oxygen, nitrogen or sulfur atom.

Particularly useful heterocyclic compounds are those described in EP-A-360390, EP-A-429366, EP-A-430771, EP-A-499313, EP-A-514273, EP-A-514274, EP-A-514275, EP-A-514276, EP-A-520555, EP-A-528495, EP-A-532456, EP-A-545478, EP-A-558156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099 or WO-A-93/09116. Preferably, the compound comprising at least one nitrogenous heterocycle is a 2-tricyclyl-2-aminoethane derivative, a spirolactam derivative, a quinuclidine derivative, an azacyclic derivative, an aminopyrrolidine derivative, a piperidine derivative, an aminoazaheterocycle, or an isoindole derivative.

Exemplary other heterocyclic compounds include oxygen-containing or sulfur-containing heterocyclic compounds, such as furan derivatives, benzofuran derivatives, thiophene derivatives and benzothiophene derivatives, optionally containing nitrogenous substituents, such as the heterocyclic compounds described in U.S. Pat. No. 4,931,459, U.S. Pat. No. 4,910,317 and EP-A-299457, and, more especially, alkoxy- and/or aryloxytetrazolylbenzofurancarboxamides or alkoxy- and/or aryloxytetrazolylbenzothiophene carboxamides.

Exemplary compounds containing a nitrogen atom bonded directly or indirectly to a benzene ring are those described in EP-A-522808, WO-A-93/01165 and WO-A-93/10073.

Exemplary salts of cations which are well suited according to the invention include, in particular the salts of strontium, magnesium, lanthanides having an atomic number ranging from 57 to 71, cobalt, nickel, manganese, barium, yttrium, copper, tin, rubidium, lithium and zinc.

These salts can be, for example, carbonates, bicarbonates, sulfates, glycerophosphates, borates, chlorides, nitrates, acetates, hydroxides or persulfates, as well as salts of α-hydroxy acids (citrates, tartrates, lactates or malates) or of the fruit acids in general, or, alternatively, salts of amino acids (aspartate, arginate, glycocholate or fumarate) or salts of fatty acids (palmitate, oleate, caseinate or behenate). The salt is preferably one of strontium, manganese, yttrium or magnesium nitrate, strontium, manganese, yttrium or magnesium borate, strontium, manganese or magnesium chloride or magnesium, manganese or strontium sulfate. More preferably, these salts are strontium chloride or strontium nitrate.

The substance P antagonists can be synthesized or extracted from natural sources (plants or animals). In particular, *Iridacea* extracts can be used, such as those from *Iris pallida*, or filamentous bacterium extracts.

In the compositions according to the invention, the substance P antagonist is preferably formulated in an amount ranging from 0.000001% to 20% of the total weight of the composition and, in particular, in an amount representing from 0.0001% to 15% of the total weight of the composition. For salts, an amount constituting from 0.01% to 20% of the total weight of the composition and, in particular, an amount constituting from 0.1% to 15% of the total weight of the composition and, more preferably, from 0.5% to 8% thereof is advantageously incorporated. For peptide derivatives and non-peptide derivatives containing a heteroatom, the amounts used advantageously range from 0.000001% to 10% of the total weight of the composition and preferably from 0.0001% to 5%.

The compositions according to the invention can be formulated in all of the pharmaceutical dosage forms normally employed for topical application onto the skin and/or the scalp, in particular solutions, which may be aqueous, alcoholic or aqueous/alcoholic, or dispersions of the lotion or serum type, emulsions with a liquid or semi-liquid consistency of the milk type, obtained by dispersion of a fatty phase in an aqueous phase (O/W) or vice versa (W/O), or suspensions or emulsions with a soft consistency of the cream, foam or gel type, or, alternatively, microgranules, or vesicular dispersions of ionic and/or non-ionic type. These compositions can, in addition, be provided in the form of a stick (solid product) or of a product pressurized by a propellant agent (aerosol). They are, moreover, prepared via the conventional techniques.

The amounts of the different constituents of the compositions according to the invention are those conventionally used in the fields under consideration.

When the composition of the invention is an emulsion, the proportion of the fatty phase can range from 5% to 80% by weight, and preferably from 5% to 50% by weight, with respect to the total weight of the composition. The oils, the emulsifiers and the coemulsifiers used in the composition in the emulsion form are selected from among those conventionally used in the cosmetics field. The emulsifier and the coemulsifier are present, in the composition, in a proportion ranging from 0.3% to 30% by weight, and preferably from 0.5% to 20% by weight, with respect to the total weight of the composition. The emulsion can, in addition, contain lipid vesicles.

When the composition of the invention is an oily gel or solution, the fatty phase can constitute more than 90% of the total weight of the composition.

In known manner, the cosmetic and/or dermatological composition of the invention can also contain adjuvants and additives which are conventional in these fields, such as hydrophilic or lipophilic gelling agents, hydrophilic or lipophilic active principles, preservatives, antioxidants, solvents, fragrances, fillers (talc), screening agents, bactericides, odor absorbers and coloring materials. The amounts of these different adjuvants and additives are those conventionally used in the cosmetics field and, for example, range from 0.01% to 20% of the total weight of the composition. These adjuvants and additives, depending on their nature, can be introduced into the fatty phase, into the aqueous phase and/or into the lipid spherules.

Exemplary oils according to the invention include mineral oils (liquid petrolatum), vegetable oils (liquid fraction of karite butter, sunflower oil), animal oils (perhydrosqualene), synthetic oils (purcellin oil), silicone oils (cyclomethicone) and fluorinated oils (perfluoropolyethers). Fatty alcohols and fatty acids (stearic acid), as well as waxes (beeswax, paraffin wax or carnauba wax), can be added to these oils.

Exemplary emulsifiers which are suitable according to the invention, include glyceryl stearate, polysorbate 60 and the PEG-6/PEG-32/glycol stearate mixture marketed under the trademark Tefose®63 by Gattefosse.

Exemplary solvents which are suitable include the lower alcohols, in particular ethanol and isopropanol.

Exemplary hydrophilic gelling agents include carboxyvinyl polymers (carbomer), acrylic copolymers such as acrylate/alkyl acrylate copolymers, polyacrylamides, polysaccharides such as hydroxypropylcellulose, natural gums and clays and exemplary lipophilic gelling agents include modified clays such as bentones, metal salts of fatty acids such as aluminum stearates, and hydrophobic silica.

Representative hydrophilic active principles include proteins or protein hydrolysates, amino acids, polyols, urea, allantoin, sugars and sugar derivatives, water-soluble vitamins, starch, bacterial or plant extracts, such as those from Aloe vera, and hydroxy acids (citric, lactic, glycolic or tartaric and fruit acids in general).

And exemplary lipophilic active principles include retinol (vitamin A) and derivatives thereof, essential fatty acids, ceramides, essential oils or salicylic acid and derivatives thereof (5-(n-octanoyl)salicylic). In particular, salicylic, lactic and acetic acids are especially useful as antiseptics.

Other active principles which are well suited for formulation according to the invention include:

(1) antibacterials, such as clindamycin phosphate, erythromycin or antibiotics from the tetracycline class;

(2) agents for combating parasites, in particular metronidazole, crotamiton or pyrethrinoids;

(3) antifungals, in particular compounds belonging to the imidazole class, such as econazole, ketoconazole or miconazole or salts thereof, polyene compounds, such as amphotericin B, compounds of the allylamine family, such as terbinafine, or, alternatively, octopirox;

(4) steroidal anti-inflammatory agents, such as hydrocortisone, betamethasone valerate or clobetasol propionate, or non-steroidal anti-inflammatory agents, such as ibuprofen and salts thereof, diclofenac and salts thereof, acetylsalicylic acid, acetaminophen or glycyrrhetinic acid;

(5) anaesthetic agents, such as lidocaine hydrochloride and derivatives thereof;

(6) agents for combating or scavenging free radicals, such as α-tocopherol (vitamin E) or esters thereof, superoxide dismutases, certain metal chelating agents or ascorbic acid and esters thereof;

(7) antiseborrhoeics, such as progesterone.

The substance P antagonists of the invention can advantageously be combined with active principles or species normally eliciting an irritant side-effect and commonly employed in the field of deodorants. The presence of a substance P antagonist in a deodorant composition containing an active principle normally eliciting an irritant effect makes it possible to greatly decrease, indeed eliminate, this irritant effect. Thus, it is envisaged to formulate a small amount of the antiperspirant agents of the prior art in combination with one or more antiperspirant agents of the invention.

The present invention also features a cosmetic and/or dermatological treatment regimen, according to which a composition as described above containing, as antiperspirant agent, at least one substance P antagonist in a cosmetically or dermatologically acceptable medium is topically applied onto the skin.

The cosmetic treatment of the invention is advantageously carried out by applying the hygiene or cosmetic compositions as described above according to the usual techniques for the use of these compositions. For example: application of creams, gels, serums, lotions or milks.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

Aqueous antiperspirant cream (oil/water) (CTFA nomenclature)

Phase A: fatty

| (a) | Cetearyl alcohol (fatty substance, gelling agent) | 4% |
|---|---|---|
| (b) | Glyceryl stearate (fatty substance, gelling agent) | 2.5% |
| (c) | Steareth-25 (emulsifier) | 1.05% |
| (d) | Stearyl alcohol (fatty substance, gelling agent) | 1.05% |
| (e) | Ceteareth-33 (emulsifier) | 1% |
| (f) | Dimethicone | 1% |
| (g) | Ceteth-20 (emulsifier) | 0.4% |
| (h) | Preservative | q.s. |

Phase B: aqueous

| (i) | Water | q.s. for 100% |
|---|---|---|
| (j) | Strontium chloride (antiperspirant) | 13% |
| (k) | Preservative | q.s. |

Phase C: active principle

| (l) | Fragrance | q.s. |
|---|---|---|
| (m) | Bactericide | q.s. |

Phase D

| (n) | Talc | 1% |
|---|---|---|

Procedure: The phase B was heated to 70°–80° C., with stirring. The phase A was heated to 70°–80° C. When the two phases were completely homogeneous, A was incorporated into B, with vigorous stirring for 10 min. The mixture was cooled with less vigorous stirring. The premix phase C was added at 45° C. The mixture was vigorously stirred for 5 min. The mixture was cooled with less vigorous stirring. The phase D was slowly incorporated at approximately 30° C. Cooling was continued to room temperature.

A soft and smooth cream was obtained, with a powdering effect on spreading, which provided effective protection against perspiration.

EXAMPLE 2

Anhydrous antiperspirant cream (CTFA nomenclature)

Phase A

| (a) | Stearalkoniuxn hectorite (gelling agent) | 4.2% |
|---|---|---|
| (b) | Propylene carbonate (suspending agent) | 1.4% |
| (c) | Caprylic/capric triglycerides | 29.4% |
| (d) | Dimethicone | 5% |
| (e) | Isohexadebane (solvent) | q.s. for 100% |

Phase B

| (f) | Barium chloride (antiperspirant) | 15% |
|---|---|---|
| (g) | Talc | 1% |

Phase C

| (h) | Fragrance | q.s. |
|---|---|---|

Phase D

| (i) | Talc | 6% |
|---|---|---|

Procedure: The compounds of the phase A were mixed at room temperature. The phase C was then incorporated, still at room temperature. When the mixture was homogeneous, B and D were slowly incorporated.

The cream obtained was particularly smooth, non-greasy and non-sticky and provided, because of its dry effect, a feeling of greater security with respect to axillary dampness.

EXAMPLE 3

Aerosol (CTFA nomenclature)

Phase A

| (a) | Cyclomethicone | q.s. for 100% |
|---|---|---|
| (b) | Quaternium-18 bentonite | 3% |
| (c) | Triethyl citrate | 7% |
| (d) | Dimethiconol | 1.4% |
| (e) | Isopropyl palmitate | 6% |

Phase B

| (f) Strontium nitrate (antiperspirant) | 15% |
|---|---|

Phase C

| (g) | Talc | 1.5% |
|---|---|---|

Procedure: The ingredients of the phase A were mixed while cold. The antiperspirant and then the talc were slowly added. Vigorous mixing was carried out in order to obtain a homogeneous suspension. The latter could then be pressurized in the following manner: 13% of dispensable and 87% of compressed or liquefied gas.

The dispensable delivered leaves a smooth and powdery effect on the skin, providing protection against perspiration.

EXAMPLE 4

Compact powder

| (a) | Magnesium chloride (antiperspirant) | 5% |
|---|---|---|
| (b) | Talc | q.s. for 100% |
| (c) | Kaolin | 10% |

-continued

| (d) | Strontium chloride (antiperspirant) | 15% |
|---|---|---|
| (e) | Fragrance | 0.30% |

EXAMPLE 5

Stick

| (a) | Barium chloride (antiperspirant) | 10% |
|---|---|---|
| (b) | Stearyl alcohol | 24% |
| (c) | PEG-400 distearate | 6% |
| (d) | Hydrocarbon wax | 4% |
| (e) | Cyclomethicone | 46% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for effecting at least one of preventing or controlling cutaneous perspiration in a human subject, comprising topically applying to the skin of an individual in need of such treatment, an effective antiperspirant amount of at least one substance P antagonist.

2. The method as defined by claim 1, wherein said at least one substance P antagonist provides for at least one of (i) a decrease in the extravasation of the plasma through the vascular wall induced by capsaicin or by an antidromic nerve stimulation, or (ii) inhibition of the contraction of the smooth muscles induced by the administration of substance P.

3. The method as defined by claim 1, wherein said at least one substance P antagonist is selected from the group consisting of a peptide, a compound which comprises at least one heterocycle, a nitrogenous compound which comprises at least one benzene ring, a salt of a monovalent, divalent or trivalent cation, an extract of plant or animal origin, and a mixture thereof.

4. The method as defined by claim 3, wherein said at least one substance P antagonist is sendide or spantide II.

5. The method as defined by claim 3, wherein said at least one substance P antagonist is selected from the group consisting of a 2-tricyclyl-2-aminoethane derivative, a spirolactam derivative, a quinuclidine derivative, an azacyclic derivative, an aminopyrrolidine derivative, a piperidine derivative, an aminoazaheterocycle and an isoindole derivative.

6. The method as defined by claim 3, wherein said at least one substance P antagonist is selected from the group consisting of an oxygen-containing or sulfur-containing heterocyclic compound which heterocyclic compound is in turn selected from the group consisting of from furan derivatives, benzofuran derivatives, thiophene derivatives, benzothiophene derivatives, tetrazolylbenzofurancarboxamides and tetrazolylbenzothiophenecarboxamides.

7. The method as defined by claim 3, wherein said at least one substance P antagonist is a salt selected from the group consisting of salts wherein the cation(s) contained therein is (are) selected from the group consisting of barium, magnesium, strontium, yttrium, gadolinium, manganese, zinc, cobalt and combinations thereof and the anions is (are) selected from the group consisting of chloride, carbonate, bicarbonate, borate, nitrate, hydroxide, sulphate and persulfate, or said substance P antagonist is selected from the group consisting of a salt of a fruit acid, a salt of an amino acid and a salt of a fatty acid.

8. The method as defined by claim 3, wherein said at least one substance P antagonist is a strontium salt.

9. The method as defined by claim 3, wherein said at least one substance P antagonist is selected from the group consisting of strontium chloride, strontium nitrate, an Iris extract and a filamentous bacterium extract.

10. The method as defined by claim 1, comprising coadministering to said human subject at least one additional active agent selected from the group consisting of an antibacterial active agent, an active agent for combating parasites, an antifungal active agent, an anti-inflammatory active agent, an anaesthetic active agent, an active agent for combating free radicals and an antiseborrhoeic active agent.

11. An antiperspirant composition of matter suited for at least one of preventing and controlling cutaneous perspiration in a human subject, which composition comprises an effective antiperspirant amount of at least one substance P antagonist, contained in a cosmetically/dermatologically acceptable, topically applicable medium therefor.

12. The antiperspirant composition as defined by claim 11, said at least one substance P providing for at least one of (i) a decrease in the extravasation of the plasma through the vascular wall induced by capsaicin or by an antidromic nerve stimulation, and (ii) an inhibition of the contraction of the smooth muscles induced by the administration of substance P.

13. The antiperspirant composition as defined by claim 11, wherein said at least one substance P antagonist is selected from the group consisting of a peptide, a compound which comprises at least one heterocycle, a nitrogenous compound which comprises at least one benzene ring, a salt of a monovalent, divalent or trivalent cation, an extract of plant or animal origin, and a mixture thereof.

14. The antiperspirant composition as defined by claim 13, wherein said at least one substance P antagonist is sendide or spantide II.

15. The antiperspirant composition as defined by claim 13, wherein said at least one substance P antagonist is selected from the group consisting of a 2-tricyclyl-2-aminoethane derivative, a spirolactam derivative, a quinuclidine derivative, an azacyclic derivative, an aminopyrrolidine derivative, a piperidine derivative, an aminoazaheterocycle and an isoindole derivative.

16. The antiperspirant composition as defined by claim 13, wherein said at least one substance P antagonist is selected from the group consisting of an oxygen-containing or sulfur-containing heterocyclic compound which heterocyclic compound is in turn selected from the group consisting of furan derivatives, benzofuran derivatives, thiophene derivatives, benzothiophene derivatives, tetrazolylbenzofurancarboxamides and tetrazolylbenzothiophenecarboxamides.

17. The antiperspirant composition as defined by claim 13, wherein said at least one substance P antagonist salt, wherein the cation(s) comprised in said salt is (are) selected from the group consisting of a barium, magnesium, strontium, yttrium, gadolinium, manganese, zinc, cobalt and combinations thereof and the anion(s) contained in said salt is (are) selected from the group consisting of chloride, carbonate, bicarbonate, borate, nitrate, hydroxide, sulphate and persulfate, or said substance P antagonist salt is selected from the group consisting of a salt of a fruit acid, a salt of an amino acid and a salt of a fatty acid.

18. The antiperspirant composition as defined by claim 13, wherein said at least one substance P antagonist is a strontium salt.

19. The antiperspirant composition as defined by claim 13, wherein said at least one substance P antagonist is selected from the group consisting of strontium chloride, strontium nitrate, an Iris extract and a filamentous bacterium extract.

20. The antiperspirant composition as defined by claim 11, further comprising an at least one additional active agent selected from the group consisting of an antibacterial active agent, an agent for combating parasites, an antifungal active agent, an anti-inflammatory active agent, an anaesthetic active agent, an active agent for combating free radicals, an antiseborrhoeic active agent, an odor absorber, a fragrance and an antiseptic.

21. The antiperspirant composition as defined by claim 11, wherein said at least one substance P antagonist comprises from 0.000001% to 20% of the total weight thereof.

22. The antiperspirant composition as defined by claim 21, wherein said at least one substance P antagonist comprises from 0.0001% to 15% of the total weight thereof.

23. The antiperspirant composition as defined by claim 11, which further comprises a normally skin-irritating amount of at least one skin irritant.

24. The antiperspirant composition as defined by claim 11, which is selected from the group consisting of a lotion, suspension, serum, emulsion, milk, cream, gel, powder, microcapsules, microparticles, vesicular dispersion, solution, foam, aerosol, and a stick.

* * * * *